United States Patent
Gerfin et al.

(10) Patent No.: US 7,800,034 B2
(45) Date of Patent: Sep. 21, 2010

(54) DAZZLE PROTECTION UNIT FOR A PORTABLE DAZZLE PROTECTION DEVICE INCLUDING A LIGHT CAPTURING ELEMENT GUIDING LIGHT TO AT LEAST ONE SENSOR

(75) Inventors: Tobias Gerfin, Oberrieden (CH); Kaspar Cottier, Jona (CH)

(73) Assignee: Optrel AG, Wattwil (CH)

( * ) Notice: Subject to any disclaimer, the term of this patent is extended or adjusted under 35 U.S.C. 154(b) by 433 days.

(21) Appl. No.: 11/764,553

(22) Filed: Jun. 18, 2007

(65) Prior Publication Data
US 2007/0289049 A1 Dec. 20, 2007

(30) Foreign Application Priority Data
Jun. 20, 2006 (CH) ...................... 0994/06

(51) Int. Cl.
*G01J 1/20* (2006.01)
*G02F 1/1335* (2006.01)

(52) U.S. Cl. ...................... 250/201.1; 349/14
(58) Field of Classification Search .............. 250/201.1, 250/214 B, 205; 349/14; 359/601
See application file for complete search history.

(56) References Cited

U.S. PATENT DOCUMENTS

| 5,959,705 A | 9/1999 | Fergason |
| 6,204,974 B1 | 3/2001 | Spitzer |
| 6,302,100 B1 | 10/2001 | Vandenberg |
| 7,343,060 B2 * | 3/2008 | Ohtsu et al. ................... 385/14 |
| 2005/0007667 A1 | 1/2005 | Fergason |
| 2005/0097648 A1 | 5/2005 | Ackermann |

FOREIGN PATENT DOCUMENTS
WO 2005/009309 2/2005

* cited by examiner

*Primary Examiner*—Thanh X Luu
(74) *Attorney, Agent, or Firm*—Rankin, Hill & Clark LLP (57) ABSTRACT

A dazzle protection unit (1) for a portable dazzle protection device that includes an optical dazzle protection filter (3) and at least one sensor (5) for the sensing of incident light and for controlling the translucency of the filter (3). In doing so, the dazzle protection unit (1) includes a light capturing element (4), which captures incident light on a light capturing surface area (12) and conducts it to the at least one sensor (5). The light capturing element (4) preferably captures the light from several areas located at a distance from one another on a front side of the dazzle protection unit (1). Means (8) for coupling light into the light capturing element (4) are situated at a distance from one another.

18 Claims, 4 Drawing Sheets

DAZZLE PROTECTION UNIT FOR A PORTABLE DAZZLE PROTECTION DEVICE INCLUDING A LIGHT CAPTURING ELEMENT GUIDING LIGHT TO AT LEAST ONE SENSOR

BACKGROUND OF THE INVENTION

The invention is related to the field of dazzle or glare protection devices, as are utilised, for example, in welders' head protection masks, and in particular to an auto-darkening dazzle protection unit for a portable dazzle protection device.

DESCRIPTION OF RELATED ART

Dazzle or glare protection units for portable dazzle protection devices such as protection masks and protection goggles are generally known. Modern dazzle protection devices comprise auto-darkening electro-optical filters, for example, with a liquid crystal element, the translucency of which is adapted manually or automatically. For this purpose, it is possible to measure incident light with a sensor. There is a certain risk that the surface of the sensor, or a protection window in front of the sensor, gets contaminated with dirt or else is temporarily in the shade of the light to be detected. In such cases it is possible that the sensor misses detecting a welding process, which in turn may lead to damage to the eyes of the user. Some manufacturers have therefore started to equip their dazzle protection units with several, for example, with 4 sensors.

US 2005/0007667 A1 discloses a dazzle protection device in which fibre optic light conductors lead incident light to a sensor. A saw-tooth like structure of the fibre optic light conductor is to couple light into it. However it also couples light out of the conductor.

US 2005/0097648 A1 discloses a dazzle protection device in which a UV converter is separated from a sensor by an optical waveguide: UV light in a fluorescent converter layer is converted into visible light in the near infrared range, conducted through a lens to an optical waveguide, and thus to the sensor.

BRIEF SUMMARY OF THE INVENTION

It is therefore the objective of the invention to create a dazzle protection unit for a portable dazzle protection device of the type mentioned at the beginning, which makes possible an improved and more robust sensing of the light with simultaneously low technical effort. It is a further objective of the invention to provide a simple to adapt light sensing system, which is capable of being adjusted in accordance with different work situations.

The dazzle protection unit for a portable dazzle protection device includes an optical dazzle protection filter and at least one sensor for sensing incident light and for controlling the translucency of the filter in accordance with the sensed amount of light. In doing so, the dazzle protection unit comprises a light capturing element, which captures incident light within a capturing area and guides it to the at least one sensor. The surface area of the capturing area in this is larger than the surface area of the sensor. In particular, means for coupling light into the light capturing element are placed at a distance from one another. As a result of this, it becomes possible that these means for coupling in light do not obstruct one another.

The dazzle protection unit is typically utilised as an auto-darkening dazzle protection cartridge in a protection mask, such as a welders' protection mask or protection goggles. Auto-darkening dazzle protection cartridges are compact assemblies with the optical filter, power supply, sensor or sensors, and control electronics in a common housing, and as a rule they are installable in, and respectively, removable from a mask without the use tools.

The light capturing element preferably captures light from several areas at a distance from one another on a front side on the dazzle protection unit. In doing so, the convex envelope of the capturing area encloses a surface area which amounts to at least twenty times or at least ten times the surface area of the at least one sensor. As a result of this greater coverage, the measurement of the incident amount of light becomes less dependent on local darkening or dirt contamination. The capturing area furthermore may also comprise several areas separated from one another, and from which areas the incident light is guided to the same sensor. In this case, other areas of the light capturing element are covered with respect to the incident light. Nonetheless, as a result of these several capturing areas being at a distance from one another, when one of them is darkened, the other one still captures a sufficient amount of light, in order to be capable of reliably controlling the filter with the help of, for example, a flicker circuit.

The surface area of the capturing area preferably amounts to more than five times or at least twice the surface area of one of the assigned sensors, and in particular more than ten times or more than twenty times or more than fifty times the surface area of the sensor.

The light capturing element preferably includes means for deflecting the incident light to the at least one sensor through internal reflection. These means, for example, are light conducting structures, in particular indentations on the light capturing element. These serve, in particular, for coupling in or for guiding in light from the outside into the light capturing element and for the uncoupling or guiding out of light to one or to several sensors. In a preferred embodiment of the invention, the means for deflecting are outlet prisms and or inlet prisms, which extend from an outside part, in particular from an external side of the light capturing element, into the light capturing element. With this, a constructionally particularly simple design of the light deflection is possible, that is, by conducting the light to the sensors by internal total reflection through the light capturing element. In a further embodiment of the invention, the light capturing element comprises a reflective coating on the outside towards the inside, in order to improve the light conductance by means of total internal reflection. The capturing areas and the transition areas to the sensors in doing so, however, are not coated in this manner.

Preferably, the light capturing element is formed as a single piece, and on the light capturing element, for two or more sensors each, an own means for uncoupling the incident light to the corresponding sensor is formed. In this manner it is possible as well to implement a simple construction, since several sensors can be supplied with a single element.

In a further preferred embodiment of the invention, the structures for coupling the light into the light capturing element comprise a distance between one another, which distance is at least twice the local thickness of the light capturing element. The thickness is measured in the direction along a reference inlet direction, see below. The expression "local thickness" signifies the thickness in the area of the structure for coupling in. With this it is possible to effect the deflection of the captured light, without the light immediately being attenuated by an adjoining structure for coupling in, or the light being coupled out in the wrong direction by such an adjoining structure.

Furthermore, by means of at least one indentation or a hollow space, light from two opposite directions is coupled out from the light capturing element to the same sensor, wherein the light capturing element in the area of this indentation, or respectively, of this hollow space, is formed as a single piece. As a result of this, the construction is simplified as well.

Preferably, at least one of the inlet prisms comprises at least one deflection surface, which relative to a reference inlet direction, is inclined by an inclination angle of 0 to 90 degrees and in particular by 10 to 70 degrees and preferably by 35 to 50 degrees. In doing so, the reference inlet direction extends parallel to a vertical to the light capturing surface area of the light capturing element.

The inlet prisms redirect the light along a deflection direction. The deflection direction is the direction which leads from the corresponding inlet prism to an assigned sensor or outlet prism. In the case of a long stretched-out light capturing element, this is essentially the longitudinal direction along the light capturing element. In a further preferred embodiment of the invention, the prism surface is also twisted around an axis parallel to the viewing direction. With this, it is possible to control the directional sensitivity of the installation.

Preferably, in doing so at least one outlet prism is arranged opposite one of the sensors, and one or several of the inlet prisms are arranged along the light capturing element on the same sight of the light capturing element as the at least one sensor and at a distance from the at least one sensor. It is also possible, however, to arrange at least one of the sensors on one of the end surfaces of the light capturing element (and optionally to glue it together with it), either with the viewing direction of the sensor parallel to the longitudinal expanse of the light capturing element, or else vertically to it, and with a deflection of the light by slanting the end of the light capturing element. The outlet prisms may be covered, that is, enclosed in the light capturing element, and therefore may form a hollow space. By the arrangement of an outlet prism as being a part of the light capturing element, it is possible for the light capturing element to conduct light into the sensor from two sides and for it nonetheless to be constructed as a single piece.

The light capturing element preferably is a prism with a linear expanse or else rod-shaped, and made out of a light-transmissive material. The light capturing element is therefore oblong and, for example, approx. 5 to 15 to 20 times as long as it is wide.

In a dazzle protection cartridge, the light capturing element preferably extends along one side of the filter, and in particular along at least two thirds up to the entire length of this side.

In a preferred embodiment of the invention, the light capturing element is displaced along a vertical line (as seen in the usual orientation during operation, with the filter plate being vertical as well), asymmetrically to the sensors and in particular displaced downwards. The horizontal axis of symmetry extending along the light capturing element is therefore not arranged at the same height as the sensors, but somewhat lower down. Correspondingly also an edge of the housing, which encircles the capturing area of the light capturing element and which acts as a screen or cover, is arranged displaced downwards. As a result of this, the complete arrangement is mainly sensitive to light which is incident from below.

The at least one sensor is preferably glued to the light capturing element with an adhesive. In doing so, the adhesive preferably has at least approximately the same refractive index as the material of the light capturing element. Because of this, there is no air gap between the light capturing element and the sensor, which improves the light transmission, in particular because no total reflection takes place at the transition to the sensor. In a further preferred embodiment of the invention, the light capturing element in the area of the light exit to the sensor is roughened up in order to improve the uncoupling of the light.

In a preferred embodiment of the invention the light capturing element in the capturing area is shaped as a lens. The lens may be a refractive and/or a diffractive one. A refractive lens preferably is shaped cylindrically or with rotational symmetry.

The light capturing element, together with any lens functions, is preferably made as a single piece out of a transparent plastic material, such as acrylic glass, polycarbonate, etc. It is also possible that the light capturing element is formed by a transparent adhesive, which is inserted into a hollow space or a receiving opening of the dazzle protection unit and then is hardened, resp., cured. This hollow space in this case is therefore shaped as a negative or mold for the light capturing element.

In a further preferred embodiment of the invention, the dazzle protection unit includes at least two lenses, which are arranged to be displaceable and which are capable of being arranged in a first and in a second position in the beam path of the incident light. In doing so, in a first position a first aperture angle of the sensor and in a second position a second, differing aperture angle of the sensor results. This aperture angle or response or viewing angle is the spatial angle under which incident light is brought to the sensor.

The displaceable lenses may be assigned either solely to a single sensor or else several lenses may respectively be arranged in front of several capturing areas of a light capturing element. It is possible that sets of several lenses of this kind are displaceable individually or all together. In the latter case, the several lenses preferably are arranged on a common lens carrier. By moving the lens carrier, simultaneously for several sensors (or capturing areas) respectively one of several lenses of a lens set, which is assigned to the sensor, is slid in front of the sensor (or the capturing area).

In a preferred embodiment of the invention, a dazzle protection unit includes an optical dazzle or glare protection filter and at least two sensors for sensing incident light and for controlling the translucency of the filter in accordance with the amount of light sensed. In doing so, a light conducting element is assigned to each of the sensors, and light conducting elements give the assigned sensors differing aperture angles.

Preferably, at least one of the light guiding elements is a bezel with a bezel edge, wherein the bezel edge is shaped in accordance with a predefined aperture angle. Alternatively to, or in combination with this, at least one of the light conducting elements is a lens. In addition, processing electronics preferably are present, which selects the signal of one of the at least two sensors for controlling the filter. With this it is possible to adapt the viewing angle to the work situation without any mechanical measures being necessary.

A dazzle protection unit or a dazzle protection cartridge in accordance with the invention preferably, even if it is not equipped with a light capturing element, includes a recess, into which the light capturing element is able to be inserted. In this way, the dazzle protection unit is capable of being operated without any constructional change both with as well as without the light capturing element. It is also possible to provide differing light capturing elements with the same external dimensions, of which one is inserted into the recess of the dazzle protection unit, in accordance with the number of sensors and other parameters, such as the range of visibility, etc.

In a further preferred embodiment of the invention, the light capturing element surrounds a large part or the complete circumference of the filter. In doing so, it is possible to guide light, which enters into the light capturing element in an area on a first side of the filter, around the corner to a sensor on a second side of the filter. For this purpose the corners of the light capturing element preferably are slanted at an angle of 45 degrees (in case of a view vertically onto the filter, respectively, onto a front surface of the dazzle protection unit).

In a further preferred embodiment of the invention, the light capturing element is attached outside the dazzle protection cartridge, therefore not in the same housing as the filter and the sensors. In the operating condition, however, the light capturing element includes a defined position relative to the sensors of the dazzle protection cartridge. The light capturing element in this embodiment may either be attached as a separate part on the corresponding helmet, hand-shield or other holder, or else integrated into a transparent element, such as a front plate, as is utilised for the protection of the filter against contamination with dirt, and in particular it may be formed as a single piece together with the screen.

In a further preferred embodiment of the invention, the light capturing element includes conversion means for the converting of ultra-violet radiation into visible light or into infrared radiation. This can be achieved by a coating of the inlet surfaces or outlet surfaces, or by mixing the material of the light capturing element throughout with a dye which implements this conversion.

A dazzle protection unit of this kind therefore includes a basic dazzle protection unit with the filter and the at least one sensor, preferably in a common housing, wherein the light capturing element is arranged outside the basic dazzle protection unit. It is therefore possible to individually replace the light capturing element as a separate part. If the light capturing element is integrated into a front plate or protection screen, then it is possible to replace the light capturing element together with said plate or screen. The light capturing element may be designed in accordance to the variants of light capturing elements as described in the above.

BRIEF DESCRIPTION OF THE DRAWINGS

In the following, the object of the invention is explained in more detail on the basis of preferred examples of embodiments, which are illustrated in the annexed drawings. They respectively schematically depict.

The reference marks utilised in the drawings and their significance are listed in summary in the list of reference marks. On principle, in the Figures the same parts are identified with the same reference marks.

DETAILED DESCRIPTION OF THE INVENTION

Figure 1:
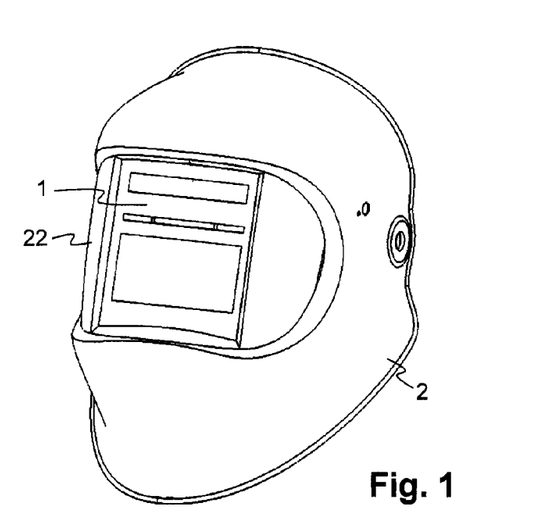
FIG. 1 a welders' protection mask.
Figure 2:
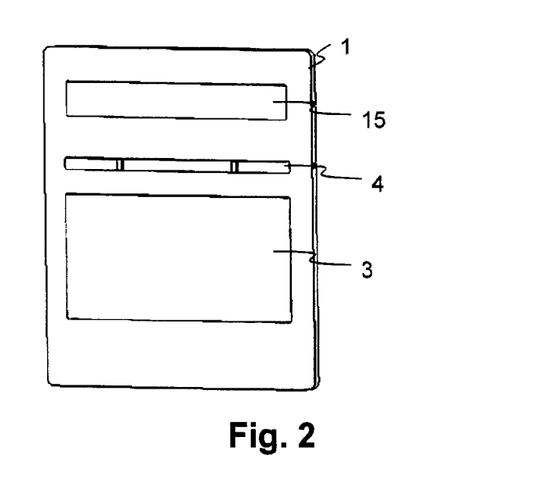
FIG. 2 a dazzle protection unit.

FIG. 1 illustrates a welders' protection mask with an inserted dazzle protection unit 1, behind a preferably interchangeable protection screen 22. FIG. 2 depicts a separate dazzle protection unit 1 with a filter 3 and a light conductor or light capturing element 4. The filter 3, for example, is an LCD filter and is controlled by control electronics integrated into the dazzle protection unit 1, i.e., in accordance with the light received from an arc is automatically darkened. For the power supply of the control electronics, the dazzle protection unit 1 may be equipped with solar cells 15 and/or a battery.

Figure 3:
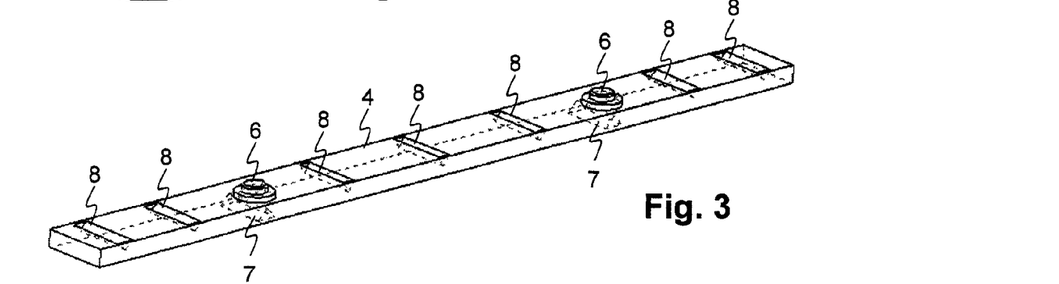
FIG. 3 a view of a light capturing element.

FIG. 3 illustrates a perspective view of a light capturing element 4 with outlet prisms 7 and inlet prisms 8 for guiding the incident light. The outlet prisms 7 are located on the areas of the light capturing element 4 situated opposite the sensors 5, 5', and the inlet prisms 8 are located on the areas facing the sensors. The light capturing element 4 consists of an optically transmissive material, such as an acrylic glass (with a refractive index of around 1.5) or of a preferably UV-resistant polycarbonate. There are two outlet prisms 4, and therefore two sensors 5, 5' are assigned to the light capturing element 4. In other embodiments of the invention it is also possible that there are more than two sensors 5, 5'. Preferably the material is tinted, so that the electronics arranged behind it are not visible.

Figure 4:
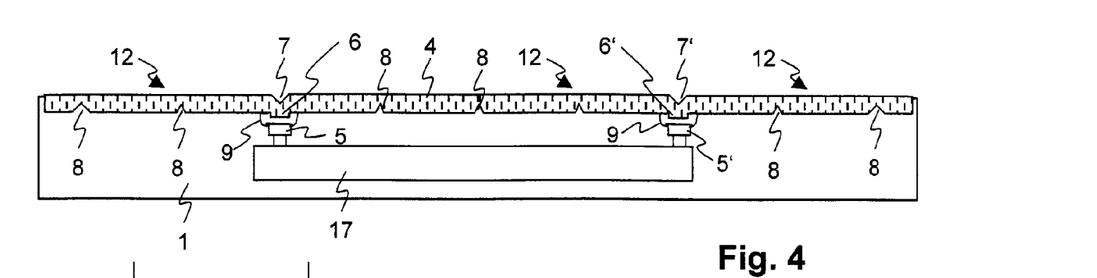
FIG. 4 a cross section of a light capturing element in a dazzle protection unit.

FIG. 4 schematically illustrates a cross section of a light capturing element 4 of a dazzle protection unit 1. Once again, the outlet prisms 7 and the inlet prisms are to be seen, as well as the sensors, 5, 5', which are arranged opposite the outlet prisms. The light capturing element 4 in the area of the sensors 5, 5' comprises extensions or protrusions 6, 6', which extend in the direction of the sensors 5, 5' and which conduct light to the sensors 5, 5'. The sensors 5, 5' are connected with the protrusions 6, 6' by means of an adhesive. The sensors 5, 5' are electrically connected with the evaluation—and control electronics 17, which, however, in the following are not depicted anymore.

Examples of dimensions for the light capturing element are: Length 100 mm; width: 8 mm; height 2 mm; inclination angle of the inlet prisms: 50 degrees for the outer inlet prisms 8 that are more distant from the sensors; 35 degrees for inlet prisms 8 situated at the sensors 5, 5'; angles of the outlet prisms: 90 degrees; distance between the inlet prisms: 14 mm; distance between the sensors: 50 mm. As a result of this, the surface area of the light capturing area is around 80 to 100 times the surface area of a sensor, therefore around 40 to 50 times the size of the sum of the surface area of the two sensors utilised in parallel. The inlet prisms are therefore at a distance from one another, i.e., between the areas of the light capturing element 4 with inlet prisms 8 also areas without inlet prisms 8 are arranged.

Figure 5:
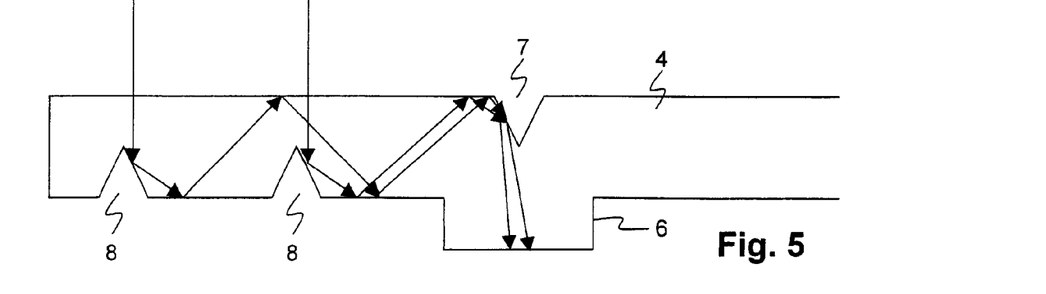
FIG. 5 a beam path in a light capturing element.

FIG. 5 schematically and enlarged illustrates a beam path, indicated by arrows, in one part of a light capturing element 4. Light incident from above, i.e., from the front side of the dazzle protection unit 1, traverses the body of the light capturing element 4. One part of the light is deflected sideways by total internal reflection on the internal sides of the inlet prisms 8 and thereupon is guided onwards in the longitudinal direction of the light capturing element 4 by total internal reflection within the light capturing element 4. In the area of one of the sensors 5, 5', the light is deflected downwards to the sensors 5, 5' by the outlet prisms 7. It becomes clear that on the basis of the spacing between the inlet prisms 8 the beam course within the light beam guide is improved—if the inlet prisms were to follow one another immediately without any distance between them, then the light would partially, as in the case of a retro-reflector, be deflected in such a manner that it would impinge on the front side with a steep angle and would thus leave the light beam conductor again.

Figure 6:
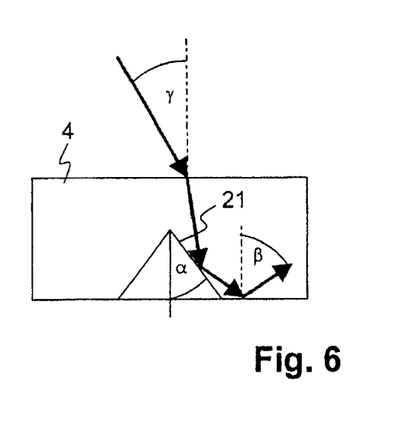
FIG. 6 a beam path at an inlet prism.

FIG. 6 illustrates the beam path on an inlet prism and how the light is coupled in by a two-fold total reflection. The inclination angle α is the angle between the reflecting prism plane and the vertical to the surface of the plane, through which the light enters into the light capturing element 4. The angle of entry of the light and the angle within the light capturing element 4, both also relative to this vertical to the surface, are designated with γ, respectively, β. It results that $$\beta = 2\alpha + a\sin(\sin\gamma/n),$$

wherein n is the refractive index in the light capturing element 4. Taking into consideration that the internal total reflection takes place in the range of 90 degrees>β>a sin(1/n), the response range of the prism 8 is adjusted by adapting α. The response range is equal to that angular range under which the light has to be incident in order to be coupled into the light beam guide 4 by the prism 8. In order to achieve a greater response range, it is also possible to utilise several prisms with differing angles of inclination, for example, several first inlet prisms 8 with a first angle of inclination and several second inlet prisms 8 with a second angle of inclination.

Figure 7:
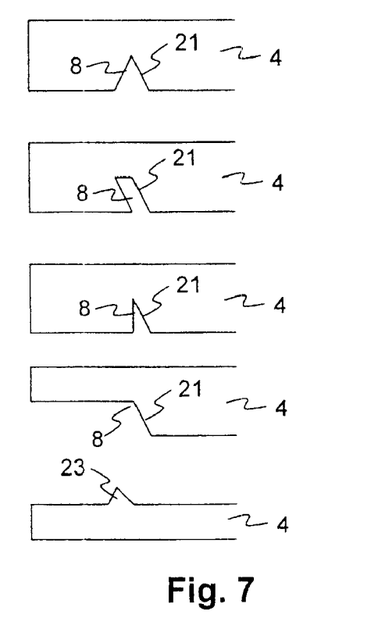
FIG. 7 various forms of inlet prisms.

FIG. 7 illustrates different forms of inlet prisms, from top to bottom: i) A prism with surface areas located opposite one another and inclined towards one another; ii) a prism with two parallel surface areas; iii) a prism with an inclined surface area and a vertical surface area relative to the light capturing inlet surface area; iv) a prism with an inclined surface area and a surface area parallel to an inlet surface area; as well as v) a front side prism as a protrusion with two surface areas protruding from the light beam conductor and inclined towards one another. The four upper variants with rear inlet prisms 8 provide the advantage, that they are less prone to contamination with dirt than the lowest variant with an inlet prism on the front side 23. These structures, in accordance with FIG. 7 may consist of individual large or macroscopic prisms, and/or of a large number of micro-prisms, such as, for example, are described in US 2001/053075 A1.

Figure 8:
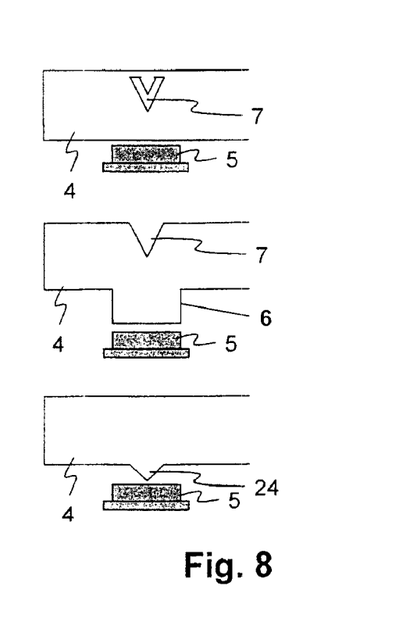
FIG. 8 various forms of outlet prisms.

FIG. 8 illustrates different further forms of outlet prisms 7, and this, from the top to the bottom: i) A prism 7 with surface areas located opposite one another and inclined towards one another, which are incorporated in the light capturing element 4 and as a result of this are protected against contamination with dirt; ii) a prism with surface areas located opposite one another and inclined towards one another, which are open towards the top; as well as iii) a prism on the surface area facing the sensor 5 with two surface areas protruding out of the light beam conductor and inclined towards one another, which therefore form a protrusion 24 as outlet prism. Here too, it is possible that macroscopic elements and/or a large number of micro-prisms are utilised. In the case of the middle variant, the light outlet surface area in front of the sensor 5 is offset by a further protrusion 6, so that the light is conducted to the sensor 5 through the further protrusion through an opening in a printed circuit board or a carrier 18 of an electronic circuit. In doing so, the sensor 5 is preferably attached to the printed circuit board itself. It is also possible of course, that a protrusion of this kind is combined with the other variants of the outlet prisms.

Figure 9:
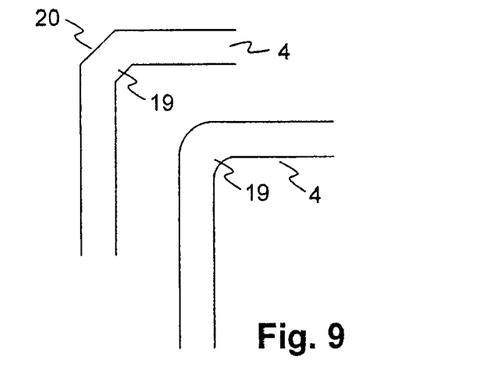
FIG. 9 various corners on light capturing elements.

FIG. 9 illustrates different corners 19 on light capturing elements 4. The light capturing element 4 comprises an oblong shape, which leads around at least one corner 19. In doing so, the external area of the corner 19 is rounded for the purpose of deflecting the light within the light capturing element 4, or else comprises a corner surface 20 which is vertical to the angle halving line of the corner 19. Light, which is captured in one leg of the light capturing element 4, in this manner is conducted around the corner 19 into the other leg, for example, to a sensor 5.

Figure 10:
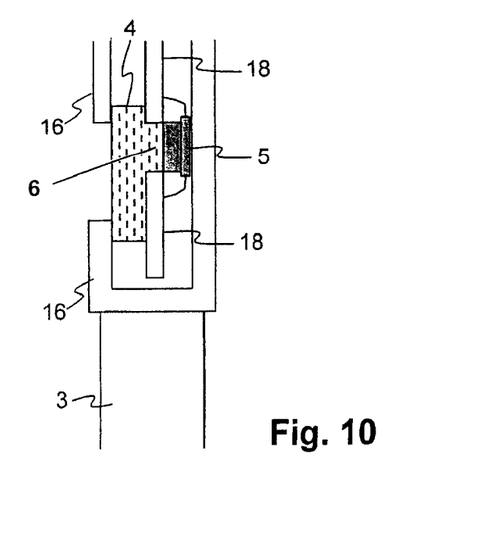
FIG. 10 a view from the side of a part of a dazzle protection unit.

FIG. 10 illustrates a view from the side of one part of a dazzle protection unit. The orientation corresponds to the orientation in operation according to the intended purpose; the viewing direction of the sensors 5 is essentially horizontal, and the dazzle protection cartridge 1 and the filter 3 are aligned approximately vertically. The light inlet surface area 12 of the light capturing element 4 is displaced downwards relative to the sensor 5, or else is at least, in a similar manner, asymmetrically covered by the edge of a bezel or covering. As a result of this, the sensor 5 is primarily supplied with light from below. In this manner, interference through ambient light is diminished.

Figure 11:
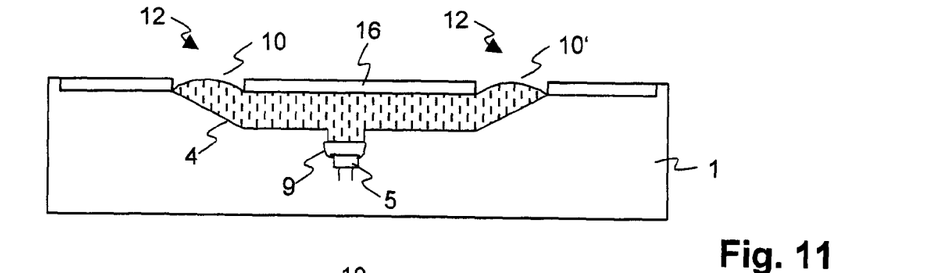
FIG. 11 an embodiment of the invention with molded-on lenses and a partially covered light capturing element.

FIG. 11 illustrates an embodiment of the invention with molded-on lenses 10 and a partially covered light capturing element 4 in a cross section from the side. Here, one part of the light capturing element 4 is covered by a covering or bezel 16, in order that only two areas act as light inlet capturing areas 12. The convex envelope of the light capturing area 12 (as viewed from above) encompasses an essentially larger surface area than the sensor surface area itself. With this, the light sensing becomes insensitive towards local shading or a local covering.

The lenses 10 preferably comprise a rotationally symmetrical surface area, therefore, for example, are spherical or non-spherical. In another embodiment of the invention, the lenses are cylindrical, and a cylindrical lens surface area of this type extends in the longitudinal direction of the light capturing element 4.

Figure 12:
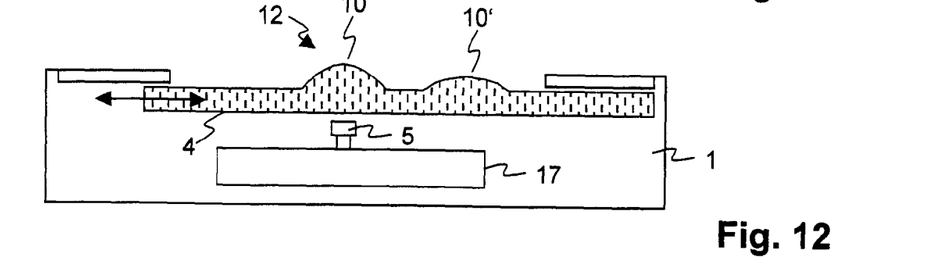
FIG. 12 a light capturing element with displaceable lens.

FIG. 12 illustrates a light capturing element with displaceable lenses 10, 10'. A carrier element or lens carrier 13 is arranged to be movable within the dazzle protection unit 1, so that it is possible for a first or a second one of the lenses 10, 10' to be slid in front of the sensor 5. The two lenses comprise differing optical characteristics, in particular focal lengths, which has the consequence that the effective viewing angle of the sensor 5 is determined by the lens.

Figure 13:
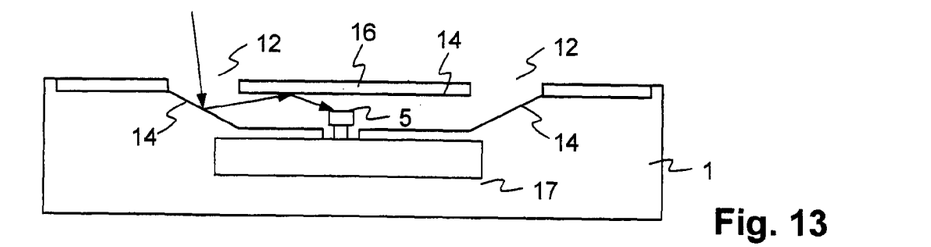
FIG. 13 an embodiment with reflective surfaces.

FIG. 13 illustrates an embodiment of the invention with reflecting surface areas. Here there is no protruding body through which the light is conducted, but rather the light is conducted through an reflectively coated hollow light conductor or a hollow space with reflecting surfaces 14 from the light capturing surface areas 12 to the sensor 5.

Figure 14:
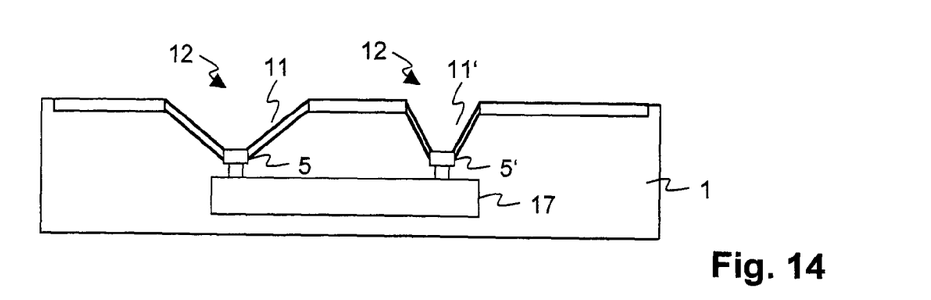
FIG. 14 a light conductor through forward bezels.
Figure 15:
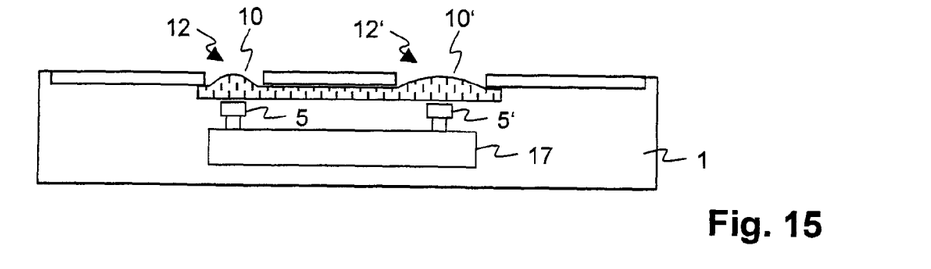
FIG. 15 a light conductor through lenses respectively assigned to the sensors.

FIG. 14 illustrates a light beam conductance through bezels with bezel edges 11, 11' placed in front of the sensors 5, 5', which restrict the viewing angle of the sensors 5, 5' to a greater or to a lesser extent. FIG. 15 illustrates an alternative light beam conductance through lenses 10, 10', each of which is assigned to one of the sensors 5, 5' in a fixed manner. In the embodiment of the invention in accordance with the FIGS. 14 and 15, the selection of different viewing angles takes place by switching-over between the sensors 5, 5'.

Figure 16:
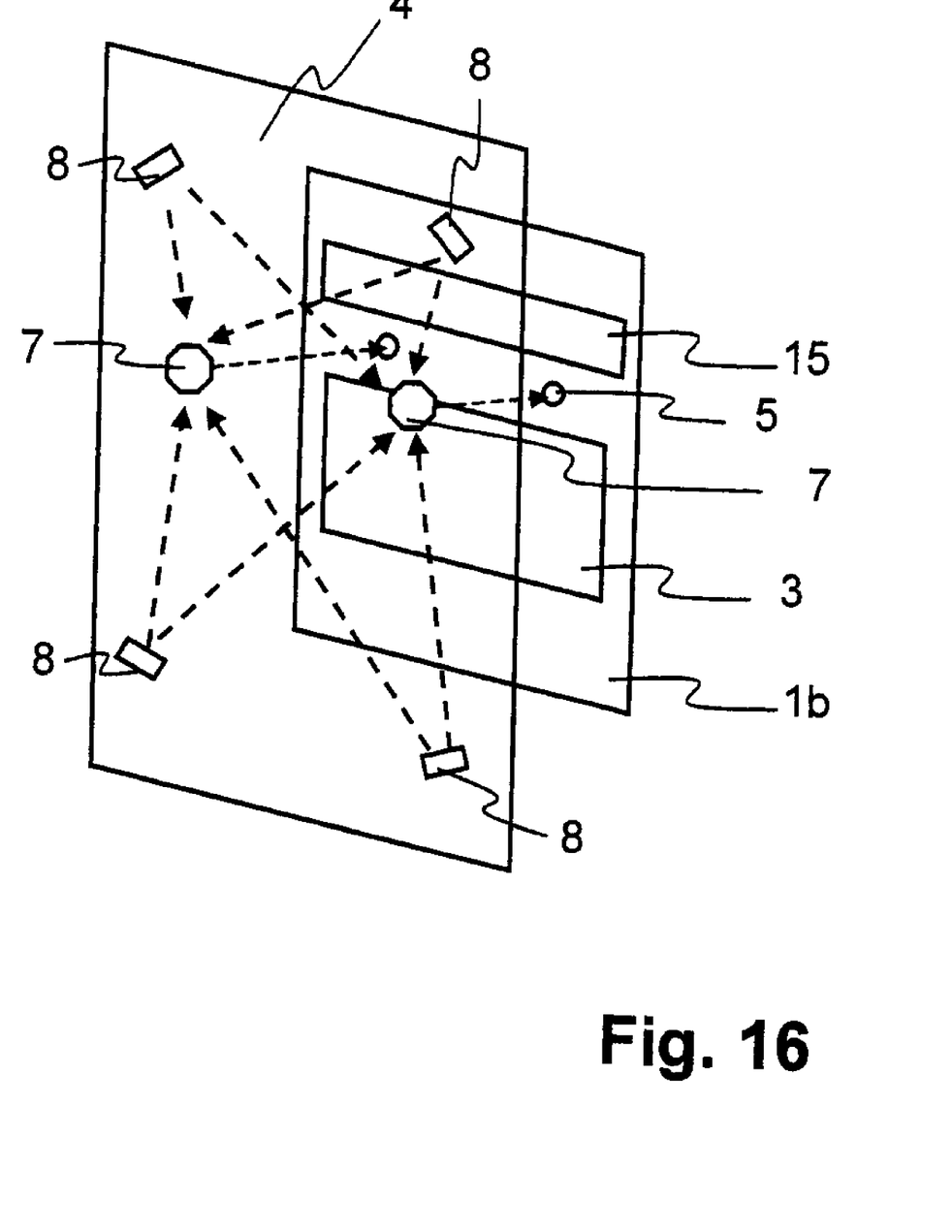
FIG. 16 a preferred embodiment of the invention with a light capturing element, which is arranged separate from and outside a dazzle protection cartridge.

FIG. 16 illustrates a preferred embodiment of the invention with a light capturing element 4 which is arranged separate from and external from the dazzle protection cartridge. The dazzle protection unit 1 for this reason consists of a dazzle protection cartridge as basic dazzle protection unit 1b, and the light capturing element 4, wherein the light capturing element 4 is a part of a different component of the protection mask 2, and in particular a part of a protection screen 22. The basic dazzle protection unit 1b therefore is constructed the same way as the dazzle protection unit 1 described in the above, with the exception, that the light capturing element 4 is not a part of the basic dazzle protection unit 1b. In FIG. 16 the course of the captured light to the sensors 5 is schematically indicated with dashed arrows. For the purpose of a better illustration, in doing so the distance between the light capturing element 4 and the basic dazzle protection unit 1b is represented as exaggeratedly large. In a preferred embodiment of the invention, the distance between the light capturing element 4 in the area of the outlet prisms 7 and the sensors 5 is as small as possible and preferably at least close to zero. The light capturing element 4 in this embodiment of the invention as well comprises inlet prisms 8 and outlet prisms 7, the mode of operation of which is the same as in the case of the embodiments described so far.

The outlet prisms 7 are arranged in correspondence with the sensors 5 of the basic dazzle protection unit 1b, i.e., in such a manner, that in the completely assembled operating condition of the light capturing element 4, resp., of the protection screen 22 and of the basic dazzle protection unit 1b in the mask, the outlet prisms 7 are located opposite the sensors 5 and thus guide light to the sensors 5. The outlet prisms 7 respectively comprise angled surface areas, which are directed towards inlet prisms 8 assigned to them and in this manner reflect light from different directions to the respective sensor 5. It is possible that the light capturing element 4 also comprises indentations as described further above.

The inlet prisms 8 are shaped analogously to those of the embodiments described so far. It is also possible, however, that they are also curved (as seen in a view from above onto the surface of the light capturing element 4), or else that they consist of several sections, which stand at an angle to one another, so that a particular one of the inlet prisms 8 conducts light to more than one of the outlet prisms 7. The inlet prisms 8 may also be distributed over the surface area of the light capturing element 4 in a linear arrangement as in FIG. 3 or else, as in FIG. 16, be distributed over the surface area of the light capturing element 4, which in this case preferably is identical with the protection screen 22 or to a partial surface area of the protection screen 22. Alternatively, however, the light capturing element 4 may be formed separately from a protection screen 22 and glued to a protection screen 22 or else arranged between the protection screen 22 and the basic dazzle protection unit 1b.

LIST OF REFERENCE MARKS

1 Dazzle protection unit
1b Basic dazzle protection unit
2 Protection mask
3 Dazzle protection filter
4 Light capturing element
5, 5',5" Sensor
6 Further protrusion
7 Outlet prism
8 Inlet prism
9 Adhesive
10 Lens
11 Bezel edge
12 Light capturing surface area
13 Lens carrier
14 Reflecting surfaces
15 Solar cell
16 Cover/Covering
17 Control electronics
18 Circuit holder, carrier
19 Corner
20 Corner surface
21 Deflecting surface
22 Protection screen
23 Protrusion for coupling-in
24 Protrusion for uncoupling

The invention claimed is:

1. A dazzle protection unit (1) for a portable dazzle protection device, wherein the dazzle protection unit (1) comprises:
an optical dazzle protection filter (3),
at least one sensor (5) for the sensing of incident light and for controlling the translucency of the filter (3) in accordance with the sensed quantity of light, and a light capturing element (4), which captures incident light on one or on several light capturing surface areas (12) and through means for the deflection of light conducts it to the at least one sensor (5),
wherein the surface area of the one or of the several light capturing surface areas (12) is larger than the surface area of the at least one sensor (5)
wherein means (8) for coupling in light into the light capturing element (4) are located at a distance from one another, and
wherein the light capturing element (4) comprises at least one protrusion (6), which conducts the light to the sensor (5) through a carrier (18) of an electronic circuit (17).

2. The dazzle protection unit (1) of claim 1, wherein two or more sensors (5, 5') are assigned to one light capturing element (4).

3. The dazzle protection unit (1) of claim 2, wherein the light capturing element (4) is formed as a single piece, and on the light capturing element (4) for two or more sensors (5, 5') each, an own associated means for uncoupling the captured light to the respective sensor (5, 5') is formed.

4. The dazzle protection unit (1) of claim 1, wherein the means for coupling in light into the light capturing element (4) comprise indentations or hollow spaces (7, 8) that function as light conducting structures, and the deflection of the light also takes place by means of internal reflection within the light capturing element (4).

5. The dazzle protection unit (1) of claim 4, wherein the means for coupling in light into the light capturing element (4) are distanced from one another by at least twice a local thickness of the light capturing element (4).

6. The dazzle protection unit (1) of claim 1, wherein the light capturing element (4) is a linearly extending or rod-like prism made from an optically transparent material.

7. The dazzle protection unit (1) of claim 6, wherein the light capturing element (4) extends in a linear manner along one side of the filter (3), and in particular along at least two thirds of this side.

8. The dazzle protection unit (1) of claim 1, wherein the light capturing element (4) comprises an oblong shape, which leads around at least one corner (19), wherein the external area of the corner (19), for the purpose of deflecting the light within the light capturing element (4), is rounded or else comprises a corner surface area (20) vertical to the line halving the angle of the corner (19).

9. The dazzle protection unit (1) of claim 1, wherein the light capturing element (4) is displaced along an axis, which axis, in the usual orientation during operation of the unit lies at least nearly vertically and in parallel to the plane of the filter (3), and which displacement relative to the sensors (5, 5') is asymmetrical and in a downward direction.

10. The dazzle protection unit (1) of claim 1, wherein the at least one sensor (5) is glued to the light capturing element (4) with an adhesive (9), wherein the adhesive exhibits at least almost the same refractive index as the material of the light capturing element (4).

11. The dazzle protection unit (1) of claim 1, wherein the light capturing element (4) in the light capturing surface area (12) is shaped as a refractive or diffractive lens (10).

12. The dazzle protection unit (1) of claim 1, further comprising a dazzle protection cartridge as basic dazzle protection unit (1b) with the filter (3) and the at least one sensor (5), wherein the light capturing element (4) is arranged outside the basic dazzle protection unit (1b), and in a configuration ready for operation in a dazzle protection device (2) comprises a defined position relative to the at least one sensor (5) and conducts the incident light to the at least one sensor (5).

13. The dazzle protection unit (1) of claim 12, wherein the light capturing element (4) is integrated into a transparent protection screen (22), and is formed as a single piece with the protection screen.

14. A transparent protection screen (22), for utilization in a portable dazzle protection device (2) with a dazzle protection unit (1) of claim 13, wherein the replacement part comprises a light capturing element (4), which in the case of an arrangement ready for operation comprises a defined position in the dazzle protection device (2) relative to the at least one sensor (5) and which conducts the incident light to the at least one sensor (5).

15. A dazzle protection unit (1) for a portable dazzle protection device, wherein the dazzle protection unit (1) comprises:
  an optical dazzle protection filter (3),
  at least one sensor (5) for the sensing of incident light and for controlling the translucency of the filter (3) in accordance with the sensed quantity of light, and a light capturing element (4), which captures incident light on one or on several light capturing surface areas (12) and through means for the deflection of light conducts it to the at least one sensor (5),
  wherein the surface area of the one or of the several light capturing surface areas (12) is larger than the surface area of the at least one sensor (5),
  wherein means (8) for coupling in light into the light capturing element (4) are located at a distance from one another,
  wherein the means for the deflection of light are outlet prisms (7) and/or inlet prisms (8), which extend from an external part of the light capturing element (4) into the light capturing element (4), and
  wherein at least one outlet prism (7) is arranged on the light capturing element (4) opposite to one of the at least one sensors (5), and one or several of the inlet prisms (8) are arranged along the light capturing element (4) on the same side of the light capturing element (4) as the at least one sensor (5) and at a distance from the at least one sensor (5).

16. The dazzle protection unit (1) of claim 15, wherein at least one of the inlet prisms (8) comprises at least one deflection surface (21), which relative to a reference inlet direction is inclined by an angle of inclination of 35 degrees to 50 degrees, wherein the reference inlet direction is parallel to a surface normal of a light capturing surface of the light capturing element (4).

17. The dazzle protection unit (1) of claim 16, wherein at least one of the inlet prisms (8) comprises a deflection surface (21) with a first angle of inclination and at least a further one of the inlet prisms (8) comprises a deflection surface (21) with a second, differing angle of inclination.

18. The dazzle protection unit (1) of claim 15, wherein the light capturing element (4) comprises protrusions (23, 24) as light conducting structures.

* * * * *